United States Patent
Steube

(10) Patent No.: US 7,354,628 B2
(45) Date of Patent: Apr. 8, 2008

(54) MEDICAL DEVICE LUBRICANT COMPRISING RADIATION CURABLE SILICON MATERIAL

(75) Inventor: Gregory Alan Steube, St. Charles, MO (US)

(73) Assignee: Covidien AG (CH)

( * ) Notice: Subject to any disclaimer, the term of this patent is extended or adjusted under 35 U.S.C. 154(b) by 323 days.

(21) Appl. No.: 10/521,937

(22) PCT Filed: Jul. 24, 2003

(86) PCT No.: PCT/US03/23136

§ 371 (c)(1),
(2), (4) Date: Jan. 24, 2005

(87) PCT Pub. No.: WO2004/009146

PCT Pub. Date: Jan. 29, 2004

(65) Prior Publication Data

US 2005/0203201 A1    Sep. 15, 2005

Related U.S. Application Data

(60) Provisional application No. 60/398,186, filed on Jul. 24, 2002.

(51) Int. Cl.
  *C08J 7/04* (2006.01)
  *C09D 183/06* (2006.01)
(52) U.S. Cl. .................. 427/515; 522/31; 522/148
(58) Field of Classification Search ............... 522/148, 522/170, 31; 427/515
See application file for complete search history.

(56) References Cited

U.S. PATENT DOCUMENTS

| | | | |
|---|---|---|---|
| 3,939,049 A | 2/1976 | Ratner et al. | 204/159.13 |
| 3,975,350 A | 8/1976 | Hudgin et al. | 260/30.4 N |
| 3,987,497 A | 10/1976 | Stoy et al. | 3/1 |
| 4,100,309 A | 7/1978 | Micklus et al. | 427/2 |
| 4,119,094 A | 10/1978 | Micklus et al. | 128/132 R |
| 4,467,073 A | 8/1984 | Creasy | 525/127 |
| 4,720,521 A | 1/1988 | Spielvogel et al. | 524/862 |
| 4,769,013 A | 9/1988 | Lorenz et al. | 604/265 |
| 4,806,430 A | 2/1989 | Spielvogel et al. | 428/450 |
| 5,091,205 A | 2/1992 | Fan | 427/2 |
| 5,260,348 A * | 11/1993 | Shepherd et al. | 522/25 |
| 5,295,978 A | 3/1994 | Fan et al. | 604/265 |
| 5,576,356 A * | 11/1996 | Leir et al. | 522/31 |
| 5,650,453 A * | 7/1997 | Eckberg et al. | 522/31 |
| 5,911,711 A | 6/1999 | Pelkey | 604/265 |
| 5,985,355 A | 11/1999 | Walther et al. | 427/2.28 |
| 6,022,050 A * | 2/2000 | Kline | 283/81 |
| 6,187,834 B1 | 2/2001 | Thayer et al. | 522/15 |
| 6,344,520 B1* | 2/2002 | Greene | 525/100 |
| 6,406,792 B1 | 6/2002 | Briquet et al. | 428/447 |
| 6,486,267 B1* | 11/2002 | Bilodeau | 525/474 |
| 6,787,490 B2* | 9/2004 | Shipp, Jr. | 442/123 |
| 2004/0209784 A1* | 10/2004 | Hardman et al. | 508/204 |

FOREIGN PATENT DOCUMENTS

| EP | 1 004 612 A1 | 5/2000 |
|---|---|---|
| EP | 1 083 205 A1 | 3/2001 |

* cited by examiner

*Primary Examiner*—Susan W. Berman

(57) ABSTRACT

The invention relates to a lubricant for medical devices. The inventive lubricant uses silicone epoxy and vinyl ether that both rapidly cure when exposed to ultraviolet light or an intense electron beam. The lubricants formulated with these components in combination with a secondary silicone component and a photoinitator offer improved performance when compared to lubricants formulated from the prior art method of using a RTV+silicone fluid materials. The speed of the UV/EB cure of the new components makes lubricants formed from them more compatible with high speed manufacturing processes by eliminating the delay of prior art lengthy cure steps.

13 Claims, 1 Drawing Sheet

MEDICAL DEVICE LUBRICANT COMPRISING RADIATION CURABLE SILICON MATERIAL

RELATED APPLICATION INFORMATION

This patent application claims priority to provisional patent application No. 60/398,186, filed in the U.S. Patent and Trademark Office on Jul. 24, 2002, the entire contents of which is incorporated herein by reference.

FIELD OF INVENTION

The invention relates to a medical device lubricant and a process for coating medical articles with the inventive lubricant. The coating is intended to reduce the force necessary to pass medical articles, such as needles, through tissue. The inventive coating reduces the drag associated within uncoated medical devices thus reducing pain associated with their use.

BACKGROUND OF INVENTION

The application of lubricious coatings to medical devices used for cutting tissue, such as hypodermic needles, surgical needles, and scalpels, has been long recognized as a method for reducing cutting forces and associated pain encountered in using these devices. The most widely recognized materials used for these coatings are silicones. Specifically, mixtures of polydimethylsiloxane (PDMS) and curable amino-functional silicone dispersion are the most commonly used silicone lubricant. Functionally, PDMS serves as a friction reducing lubricant. The amino-functional silicone dispersion cures (crosslinks) the binding of the coating to the medical device's cutting edge. These materials are available from several sources, the best known being Dow-Corning, which markets their PDMS in a range of viscosities as DC-360 Medical Fluid, and their amino-functional silicone dispersion as MDX4-4159. These products have been available for over 25 years, and have generated various methods and coating formulations for specific applications. These methods include single and two step application methods.

Unfortunately, a disadvantage of using these materials in the coating of hypodermic needles is the cure time associated with the dispersion. The dispersion is a member of a family of silicone materials known as Room Temperature Vulcanizates (RTV). In these materials, curing is triggered by exposure of the coating to atmospheric moisture. RTV silicones require small quantities of water to initiate a cure. According to Dow-Corning's product literature, curing requires 7-10 days at ambient conditions. In the prior art, the cure time can be accelerated by temperature, one example of which is the two step method described in U.S. Pat. No. 5,911,711 (the '711 patent). Unfortunately, the acceleration of the cure time disclosed in the '711 patent still inhibits the manufacturing process. While the two step coating process describe in the '711 patent can provide improved product performance by reducing penetration forces, it suffers from the need to have a long delay period between coating steps to allow partial curing.

Another method of using two coat lubricants is described in U.S. Pat. No. 5,985,355 (the '355 patent). In the '355 patent a first "leveling" coat is applied as a base coat to smooth out irregularities on the coating substrate. The base coat is followed by a lubricious top coat. Unfortunately, the two step process of the '355 patent also suffers from the need to have a delay period between coating steps to allow curing. This delay period creates manufacturing problems for products that could benefit from a two step coating.

In the high speed manufacture of hypodermic needles, needles coated by a process without a cure cycle may be exposed to the atmosphere for a brief interval and then are often packaged in a non-permeable package. Unfortunately, the lack of sufficient exposure to atmospheric moisture has been shown to extend the cure time to as much as 4-5 weeks. This extended cure time results in increased lead time manufacturing and supply problems. This increase in manufacturing lead time can potentially produce products, which in a clinical setting do not have optimum lubricant functionality and therefore increase patient discomfort.

SUMMARY OF INVENTION

The invention of the present disclosure is a lubricant for medical devices incorporating novel materials. The disadvantages of prior art methods of lubricating medical devices with extended cure times are avoided by the inventive lubricant. Unlike the prior art where the curing mechanism of these materials relies on drawing moisture from the air to initiate the cure, the inventive lubricant involves the use of rapidly curing compounds avoiding the problems of the prior art.

The rapidly curing compounds within the inventive coating are silicone epoxy and vinyl ether polymers that both rapidly cure when exposed to ultraviolet light or an intense electron beam. As shown in the attached test data, the lubricants formulated with these components offer improved performance when compared to lubricants formulated from the prior art method of using a RTV+silicone fluid materials described above. The speed of ultraviolet light or electron beam (UV/EB) curing of the new materials produces lubricants that are more compatible in high speed manufacturing processes. In particular, these materials eliminate the delay of a lengthy cure step when a two coat lubricant is desired.

In the inventive lubricant coating according to present disclosure, the silicone epoxy and vinyl ether cure to a matrix similar to an interpenetrating polymer network (IPN). This matrix tends to squeeze lower surface energy silicones to the surface, creating a two layer lubricant coating comprising a leveling base layer and an advantageous lubricious top layer coating from a single application.

BRIEF DESCRIPTION OF THE DRAWINGS

The foregoing and other features and advantages of the present invention will be more fully understood from the following detailed description of illustrative embodiments, taken in conjunction with the accompanying drawing in which.

DETAILED DESCRIPTION

Figure 1:
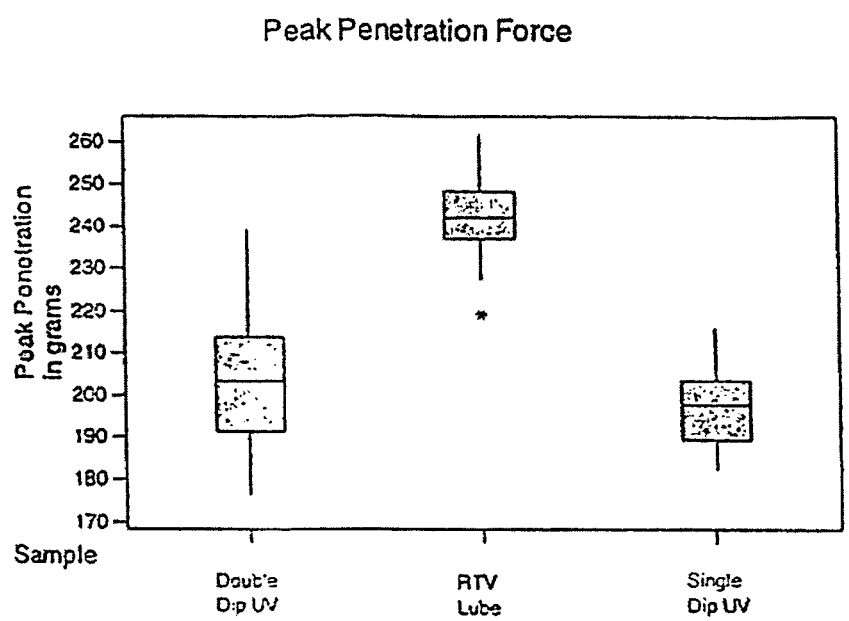
FIG. 1 is a graphical representation of the penetration force measured during a penetration of a hypodermic needle into a rubber vial stopper using a Sintech Universal Testing Machine operating at 200 mm/minute.

The instant invention provides an inventive lubricant coating and methods for coating medical devices with the inventive coating. The inventive lubricant coating provides patients with a reduction in discomfort associated with current commercially available needles. This lubricious coating can be used in other medical devices where penetration into skin surfaces or orifices can be improved by the addition of a lubricant coating.

The inventive lubricant uses ultraviolet light or electron beam (UV/EB) curable materials as an alternative to the RTV silicone dispersion described above. According to the invention, the inventive lubricant is a combination of a silicone-epoxy copolymer mixed with a cationic photoinitiator that is dispersed with vinyl ether and a further secondary silicone component. The silicone-epoxy copolymers are organo-functional polydimethylsiloxane (PDMS) polymers where methyl groups are replaced with reactive organic moieties including acrylate, oxirane, or other readily polymerizable groups. The UV/EB curable silicone copolymer component contemplated in the inventive lubricant are produced as paper release coatings by Rhodia Silicones in Rock Hill S.C., under the Silcolease® trade name. These radiation curable silicone copolymers by Rhodia include, but are not limited to, Silcolease PC-675, Silcolease PC-670, Silcolease PC-600 and Silcolease PC-601. They are epoxy modified polydimethylsiloxanes having a general formula as follows:

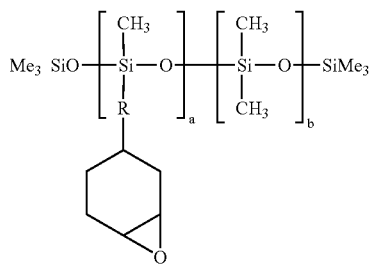

Additional radiation curable silicone-epoxy copolymer materials are produced by GE Silicones under various trade names. It is contemplated within the scope of the invention that other silicone materials that are rapidly cured by some form of irradiation may be used.

These radiation curable epoxy silicones are used with compatible iodonium-borate cationic photoinitiators such as onium type photocatalyst. In one illustrative embodiment, the onium type photocatalyst is diaryliodonium, tetrakis (pentafluorophenyl) borate salt. It is contemplated within the scope of the invention that compatible onium salt photocatalyst utilized to catalyze the curing of the epoxy silicone in the process of the present invention may be any onium salt photocatalyst known within the art. These photocatalysts include but are not limited to the following bisaryliodonium salt catalysts: bis(dodecylphenyl) iodonium hexafluoroantimonate, bis(dodecylphenyl) iodonium hexafluoroarsenate and (4-octyloxyphenyl)(phenyl) iodinium hexafluoroantimonate.

In one illustrative embodiment, the cationic photoinitiator materials used in the inventive lubricant are produced by Rhodia Silicones, Rock Hill S.C., under the Silcolease® trade name. These photoinitiators by Rhodia Silicones include but are not limited to Silcolease® PC-702, Silcolease® PC-700 and Silcolease® PC-702-30. In particular, Silcolease® PC-702 is a 20 percent iodonium borate salt cationic photoinitiator in a diacetone alcohol carrier. Because these cationic systems containing a radiation curable epoxy silicone and a photoinitiator are not subject to oxygen inhibition, they are suitable for desirable high speed radiation cure processing.

Figure 2:
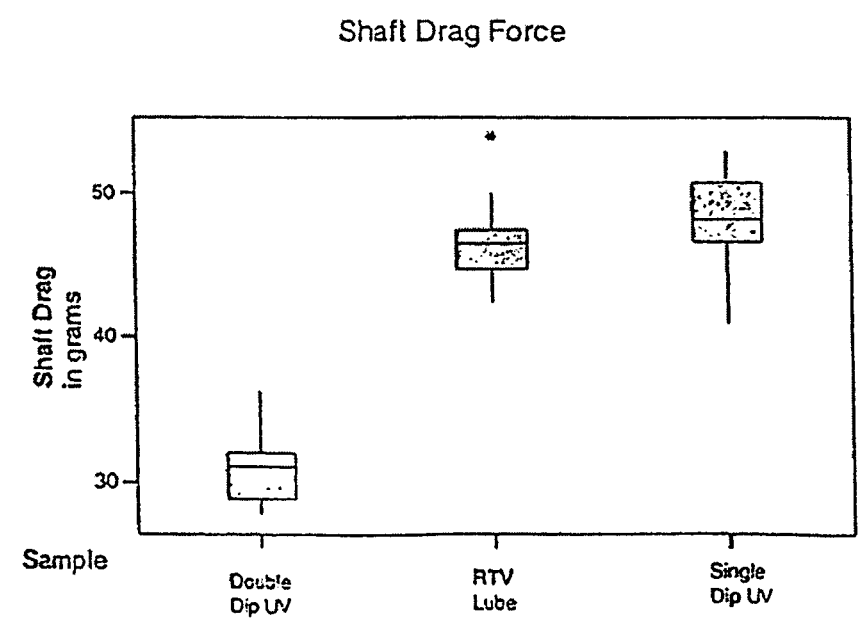
FIG. 2 is a graphical representation of the shaft drag force of the inventive lubricant in comparison to prior art lubricant.

One of the advantages of these materials lies in the rapid cure time after exposure to ultraviolet (UV) or electron beam irradiation (EB). In particular, if a two step coating is desired the rapid cure time is a manufacturing processing advantage. Single coatings of test lubricants made with these materials have also shown a reduction in penetration forces compared to prior art lubricants described above and as shown in FIG. 1 and FIG. 2. Also, as shown in FIG. 2, two step coatings utilizing this method have been shown to offer a further reduction in shaft drag forces and the reduction of peak penetration forces.

One challenge in working with these materials is that in a mixture with other materials such as a low viscosity polydimethylsiloxane (PDMS), used as a secondary silicone component, it is sometimes difficult to adequately disperse the photoinitiator such that a complete cure of the silicone-epoxy is obtained. Published literature concerning the use of these materials in paper release coatings suggests the use of UV/EB curable vinyl ethers (VE) monomers such as DDVE and CHVE, which are compounds miscible with epoxysilicone polymers. These UV/EB curable vinyl ethers undergo rapid polymerization upon irradiation in the presence of the compatible onium type catalysts. The vinyl ethers aid in dispersing the photoinitator (therefore improving curing), and also advantageously affect the properties of the inventive coating.

Vinyl ethers, which are UV curable, that are contemplated within the scope of the invention include but are not limited to monovinyl ether of 2-ethyl-1-hexanol, monovinyl ether of n-dodecanol, divinyl ether of 1-4-cyclohexanedimethanol, and the like.

In particular, some tests have indicated that the rapid cure of the vinyl ether components (faster than silicone-epoxy), can be made to cause silicone-epoxy and secondary silicone components such as PDMS to be "squeezed" to the surface of the coating. In a published report from GE Silicones entitled Novel Radiation Curable Vinyl Ether-Epoxysilicone Compositions and Coatings, which is incorporated herein by reference in its entirety, the "squeezing" phenomena is described in the context of use as a paper release coating.

This "squeezing" phenomena caused by the use of vinyl ethers has been confirmed by surface analysis that shows a silicone content at the coating surface higher than that of the coating bath as proof of this effect. One possible advantage of this squeezing effect is that the lubrication of cutting edges allow formation of a two layer coating with the base layer serving to smooth out surface roughness and the top layer serving as the primary lubricant as described in U.S. Pat. No. 5,985,355, which is incorporated herein in its entirety by reference. This squeezing effect is formulation dependent. The GE Silicones paper also describes some paper release coatings in which the phases are reversed and the surface of the coating was vinyl ether enriched.

A secondary silicone component within the inventive lubricant provides the formulation with increased lubricant properties. Secondary silicone components contemplated within the scope of the invention include but are not limited to the following: NuSil MED-361, a PDMS silicone fluid available in a range of viscosities, NuSil MED-4162, a silicone dispersion product having a silicone ingredient that is dispersed within an organic solvent. In particular, NuSil Med-4162 is a dispersion of high molecular weight polydimethylsiloxane within a xylene solution. It is contemplated within the scope of the invention that various molecular weight polydimethylsiloxanes known in the art in various solvent carriers may be used. These polydimethylsiloxanes include, but are not limited to, polymers of methyltrimethoxy silane, methyltriacetoxy silane, silicone chloride, vinyl trimethoxy silane, bis(trimethoxysilyl) propyl amine, gamma-ureidopropyl trimethoxy silane and organosilane ester tri (3-trimethoxysilyl propyl) isocyanurate, or the like.

Additional polymethyl siloxanes such as fluorosilicones are also contemplated within the scope of the invention. It is further contemplated within the scope of the invention that copolymers of various silicones may be used. These copolymers include but are not limited to NuSil MED-420, which is a copolymer consisting of dimethylsiloxane, and trifluoropropylmethylsiloxane or Dow Corning MDX4-4159, which is a dispersion of an aminofunctional dimethylsiloxane copolymer.

In an alternative illustrative embodiment an additional advantageous method of curing these materials is contemplated. The silicone-epoxy and DDVE are both sold as ultraviolet light/electron beam curable polymers. In this alternative illustrative curing method, gamma radiation is used to sterilize numerous medical devices. Gamma radiation is capable of triggering the curing of the inventive coating. Advantageously, the use of gamma radiation eliminates the need for a dedicated UV or EB curing station in the assembly process by using a product sterilization cycle to cure the lubricant applied to needles in sealed cases. The use of gamma radiation for purposes of sterilization can substantially reduce the cost and time associated with the assembly process. Gamma sterilizer radiation doses are typically in the range of about 10-30 kiloGray.

The inventive lubricant and methods of applying it to medical articles are better understood with reference to the following illustrative examples. These examples are merely intended to illustrate the inventive lubricant and should not be construed as limiting the scope of the invention. The materials used within the illustrative examples are as follows:

EXAMPLE 1

Single Coating Lubrication Method

Silcolease PC-675: A UV/EB curable silicone-epoxy copolymer from Rhodia Silicones.

Silocolease PC-702: An iodonium borate photoinitator for use as a UV/EB cure catalyst from Rhodia Silicones.

Rapi-Cure DDVE: A UV/EB curable dodecylvinylether from International Specialty Polymers.

NuSil Med-361: 350 Cst. Polydimethylsiloxane fluid from NuSil.

NuSil MED 4162: A fully cured polydimethylsiloxame copolymer dispersed in a carrier solvent.

Silocolease PC-702 works as a catalyst for both of the UV/EB curable components. It is contemplated within the scope of the invention that other sources for the materials of the novel lubricant may be used.

Formulation:

| | |
|---|---|
| NuSil MED-4162 | 5.1% |
| NuSil MED-361 | 1.5% |
| Silcolease PC-675 | 1.4% |
| Rapi-Cure DDVE | 0.5% |
| Silcolease PC-702 | 0.1% |
| Hexane | 91.4% |

In this illustrative example, the inventive lubricant was prepared by mixing the above components in the percentages listed with a compatible organic carrier solvent, Hexane. It is contemplated within the scope of the invention that any compatible organic solvent known in the art may be used. The mixture was applied by dipping a cannula into the mixture and then slowly withdrawing. Alternatively, the inventive lubricant could be applied by other methods known in the art such as spraying, padding or passing cannula through a flowing cascade. The lubricant coating on the cannula was then cured by exposure to a UV light source.

EXAMPLE 2

Two Step Coating Method

This method consists of three steps:
1. Applying a first coating of the formulation listed in the Single Coat Lubrication Method described above.
2. Curing the lubricant on the needle by exposure to a UV light source.
3. Applying a second coat of silicones dispersed in carrier solvent.

The cure step is included to insure that a solvent-based second coat will not wash away a portion of the first coat. A typical second coat would be a mixture of approximately 6% MED-361, or approximately 1% MED-361 and approximately 5% NuSil MED-4162, diluted in a carrier solvent.

EXAMPLE 3

Comparison of Penetration Forces

The following data was collected using 21 gage needles and West Co. 1888-127 Gray drug vial stoppers. The needles were penetrated into the stopper using a Sintech Universal Testing Machine operating at 200 mm/minute. The results are set forth in FIG. 1 and FIG. 2.

Although the inventive lubricant uses a variety of epoxy silicone copolymers, it is contemplated within the scope of the invention that other radiation curable silicones may be used within the inventive lubricant. Likewise, while onium type photoinitiators are used within the inventive lubricant, it is contemplated within the scope of the invention that other photoinitiators compatible with the radiation curable silicone may be used.

The foregoing has been a description of certain specific embodiments of the present disclosure. The present disclosure is not to be limited in scope by the illustrative embodiments described, which are intended as specific illustrations of individual aspects of the disclosure, and functionally equivalent methods and components are within the scope of the invention. Indeed, various modifications of the disclosure, in addition to those shown and described herein will become apparent to those skilled in the art from the foregoing description and all such modifications are included.

What is claimed is:

1. A method for lubricating hypodermic needles comprising:
   applying a coating mixture comprising a radiation curable silicone having epoxy pendant groups, a secondary silicone component other than a radiation curable silicone having epoxy pendant groups, a photoinitiator and vinyl ether to a penetrating surface of a hypodermic needle; and
   curing said coating by exposure to radiation.

2. The method according to claim 1 wherein said radiation is selected from the group consisting of: ultraviolet light, electron beam and gamma radiation.

3. The method according to claim 1 wherein said coating is applied to said hypodermic needle by at least one of: i) dipping, ii) spraying, iii) padding, and iv) passing through a flowing cascade.

4. The method according to claim 1 wherein said vinyl ether is selected from the group consisting of monovinyl ether of 2-ethyl-l-hexanol, monovinyl ether of n-dodecanol, and divinyl ether of 1, 4-cyclohexanedimethanol.

5. The method according to claim 1 wherein said photoinitiator is selected from the group consisting of diaryliodonium tetrakis (pentafluorophenyl) borate salt, bis(dodecylphenyl) iodonium hexafluoroantimonate, bis (dodecylphenyl) iodonium hexafluoroarsenate and (4-octyloxyphenyl) (phenyl) iodinium hexafluoroantimonate.

6. The method according to claim 1 wherein said secondary silicone component is selected from the group consisting of polydimethylsiloxane, polymethyltrimethoxy silane, polymethyltrianetoxy silane, poly (silicone chloride), poly (vinyl trimethoxy silane), poly [bis (trimethoxysilyl) propyl amine]. poly (gamma-ureidopropyl trimethoxy silane), an ester of tri (3-(trimethoxysilyl) propyl) isocyanurate and a poly(fluorosilicone).

7. The method according to claim 1 further comprising the step of packaging said hypodermic needle in a sealed case prior to radiating said coating.

8. A method for lubricating hypodermic needles comprising:
applying a first coating mixture comprising a radiation curable silicone, having epoxy pendant groups, a secondary silicone component other than a silicone having epoxy pendant groups, a photoinitiator and a vinyl ether to a penetrating surface of a hypodermic needle;
curing said first coating by exposure to radiation; and
applying a second coating mixture comprising a secondary silicone component other than a silicone having epoxy pendant groups, dispersed in a carrier solvent.

9. The method according to claim 8 wherein said vinyl ether in said first coating is selected from the group consisting of monovinyl ether of 2-ethyl-l-hexanol, monovinyl ether of n-dedecanol and divinyl ether of 1,4-cyclohexanedimethanol.

10. The method according to claim 8 wherein said photoinitiator in said first coating is selected from the group consisting of diaryliodonium tetrakis (pentafluorophenyl) borate salt, bis(dodecylphenyl) iodonium hexafluoroantimonate, bis(dodecylphenyl) iodonium hexafluoroarsenate and (4-octyloxyphenyl) (phenyl) iodinium hexafluoroantimonate.

11. The method according to claim 8 wherein said secondary silicone component in said first coating is selected from the group consisting of polydimethylsiloxane, polymethyltrimethoxy silane, polymethyltriacetoxy silane, poly (silicone chloride), poly (vinyl trimethoxy silane), poly [bis (trimethoxysilyl) propyl amine]. poly (gamma-ureidopropyl trimethoxy silane), an ester of tri (3-(trimethoxysilyl) propyl) isocyanurate and a poly(fluorosilicone).

12. The method according to claim 8 wherein said secondary silicone component in said second coating is selected from the group consisting of polydimethylsiloxane, polymethyltrimethoxy silane, polymethyltriacetoxy silane, poly (silicone chloride), poly (vinyl trimethoxy silane), poly [bis (trimethoxysily) propyl amine], poly (gamma-ureidopropyl trimethoxy silane), an ester of tri (3-(trimethoxysilyl) propyl) isocyanurate and a poly(fluorosilicone).

13. The method according to claim 8 wherein said secondary silicone component in said second coating is a mixture of at least two silicone components selected from the group consisting of polydimethylsiloxane, polymethyltrimethoxy silane, polymethyltriacetoxy silane, poly (silicone chloride), poly (vinyl trimethoxy silane), poly [bis (trimethoxysilyl) propyl amine], poly (gamma-ureidopropyl trimethoxy silane), an ester of tri (3-(trimethoxysilyl) propyl) isocyanurate and a poly(fluorosilicone).

* * * * *